United States Patent [19]

Sekine et al.

[11] Patent Number: 4,849,359
[45] Date of Patent: Jul. 18, 1989

[54] FISH GROWTH HORMONE POLYPEPTIDE

[75] Inventors: Susumu Sekine; Tamio Mizukami; Moriyuki Sato, all of Machida; Seiga Itoh, Sagamihara; Akiko Saito, Machida all of Japan

[73] Assignee: Kyowa Hakko Kogyo Co., Ltd., Tokyo, Japan

[21] Appl. No.: 17,630

[22] Filed: Apr. 14, 1987

Related U.S. Application Data

[62] Division of Ser. No. 750,587, Jul. 1, 1985, Pat. No. 4,689,402.

[30] Foreign Application Priority Data

Jun. 29, 1984 [JP] Japan .................. 59-134536
Oct. 12, 1984 [JP] Japan .................. 59-213360
Oct. 12, 1984 [JP] Japan .................. 59-213361
Mar. 13, 1985 [JP] Japan .................. 60-50096

[51] Int. Cl.$^4$ ............... C12N 1/20; C12N 15/00; C12N 1/00; C07H 15/12
[52] U.S. Cl. ............... 435/252.33; 435/172.3; 435/320; 536/27
[58] Field of Search ............ 435/172.3, 253, 320; 935/13; 536/27

[56] References Cited

U.S. PATENT DOCUMENTS 4,342,832 8/1982 Goeddel et al. .............. 435/172.3

OTHER PUBLICATIONS

Sekine et al., PNAS U.S.A., vol. 82, pp. 4306–4310, Jul. 1985.
Chem. Abst. vol. 95, 109144n (1981).
Chem. Abst. vol. 87, 149071c (1977).
Chem. Abst. vol. 91, 137658u (1979).
Chem. Abst. vol. 72, 76128e (1970).
Glick et al., Genetic Engineering: Applications to Agriculture, Beltsville Symposis in Agricultural Research, vol. 17, pp. 67–79 & 86–87 (1982).
Kawauchi, Nippon Nogei Kagaka Kaishi 53(11), R141–R150 (1979) Japan.

Primary Examiner—Alvin E. Tanenholtz
Attorney, Agent, or Firm—Antonelli, Terry & Wands

[57] ABSTRACT

According to the present invention, a recombinant DNA incorporated with a DNA coding for a fish growth hormone polypeptide and a microorganism containing the recombinant DNA were obtained and they can be used for mass production of the fish growth hormone polypeptide.

5 Claims, 5 Drawing Sheets

FISH GROWTH HORMONE POLYPEPTIDE

This is a divisional application of application Ser. No. 750,587, filed July 1, 1985, now U.S. Pat. No. 4,689,402.

BACKGROUND OF THE INVENTION

The present invention relates to a DNA coding for a fish growth hormone polypeptide, a recombinant DNA incorporating the DNA, a microorganism containing the recombinant DNA and a process for the production of the fish growth hormone polypeptide using the microorganism. The fish growth hormone is expected to have various uses in an industrial field of fish cultivation.

Mammalian growth hormones are produced in the pituitary gland. The activity and structure of the mammalian growth hormones are known. For example, human growth hormones have been reported in J. Am. Chem. Soc., 80, 4429 (1958) by U. J. Lewis, et al., Biochem. J., 100, 754 (1966) by A. S. Hartree; and Arch. Biochem. Biophys. (Suppl.), 1, 327 (1962) by C. H. Li, et al.

Many reports on the isolation of fish growth hormones have been published as follows.
Isolation from Tilapias
S. W. Farmer, et al., Gen. Comp. Endocrin., 30, 91 (1976)
Isolation from Sturgeons
S. W. Farmer, et al., Endocrinology, 108, 377 (1981)
Isolation from Carps
A. F. Cook, et al., Gen. Comp. Endocrin., 50, 335 (1983)

On the other hand, as for mammalian growth hormone genes, rat growth hormone gene [P. H. Seeburg, et al., Nature 270, 486 (1977)], bovine and swine growth hormone genes [P. H. Seeburg, et al., DNA, 2, 37 (1983)] and human growth hormone gene [J. A. Martial, et al., Science, 205, 602 (1979)] are already known. However, there is no report about fish growth hormone genes and a process for producing a fish growth hormone polypeptide by recombinant DNA technology using the gene.

Fish growth hormones have a stimulating effect of the growth of fish and are useful as a component of baits for fish cultivation. The amount of the growth hormone provided by the recovery from the fish pituitary gland is limited. Therefore, it has been desired that a process for providing a large amount of fish growth hormones in a low cost is developed.

SUMMARY OF THE INVENTION

The present inventors studied methods of producing fish growth hormones by recombinant DNA techniques. As the result, the present inventors have successfully recovered a DNA complementary to a fish growth hormone polypeptide and usable in the production of fish growth hormones, and produced a recombinant DNA containing the DNA and a microorganism containing the recombinant DNA. That is, a messenger RNA (mRNA) was extracted from the salmon pituitary gland and a DNA (cDNA) complementary to the mRNA was synthesized. Then, a DNA probe corresponding to the amino acid sequence around the N-terminal of the salmon growth hormone was synthesized, and a salmon growth hormone gene was cloned by selecting a cDNA which hybridized with the DNA probe. Further, the base sequence of the cDNA was determined.

The present inventors have further studied and found that a large amount of the salmon growth hormone polypeptide is formed and accumulated in a medium by culturing a microorganism containing a recombinant DNA wherein a cDNA coding for the salmon growth hormone is incorporated.

DESCRIPTION OF THE INVENTION

Figure 1:
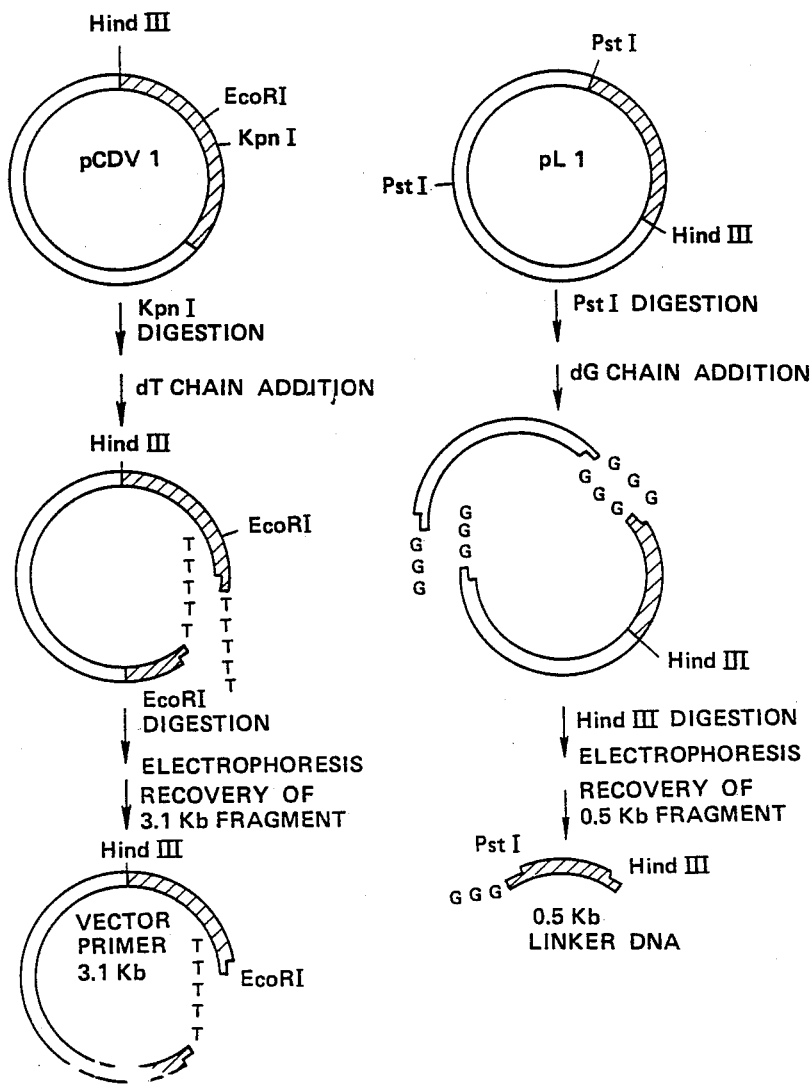
FIG. 1, (1) and (2) are a flow sheet for synthesizing cDNA by the method of Okayama-Berg and constructing a recombinant plasmid containing the cDNA.
Figure 1:
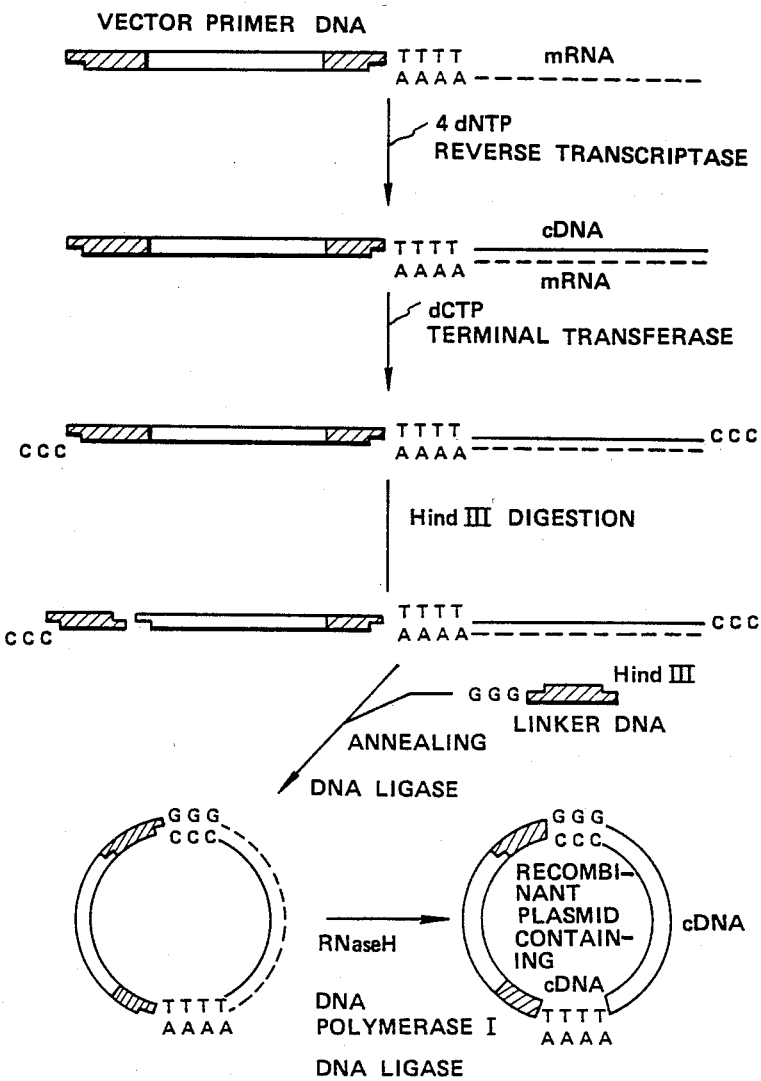

The present invention provides fish growth hormone polypeptides, for example, the polypeptide having the peptide sequence as illustrated in Table 1 or Table 2 and a process for producing the same. The polypeptide can be produced by recombinant DNA techniques as follows.

That is, an mRNA of fish growth hormone is isolated from the pituitary gland of fish and used as a template to prepare a DNA (cDNA) complementary to the mRNA, and then a recombinant plasmid incorporating the cDNA is prepared. The recombinant plasmid is incorporated in a host microorganism. The DNA and recombinant plasmid can be used for expression of fish growth hormone gene in bacteria such as *Escherichia coli*. Fish growth hormones are produced by culturing microorganisms carrying the recombinant plasmid.

Therefore, in addition the present invention provides a DNA coding for fish growth hormone polypeptide, a recombinant DNA incorporating the DNA and a microorganism containing the recombinant DNA.

The DNA and recombinant plasmid of the present invention are prepared by the following general method.

Whole RNA Is prepared from the pituitary gland of a salmon (*Oncorhynchus keta*) and passed through an oligo dT cellulose column to isolate RNA having polyadenylic acid [poly(A)RNA]. A double stranded DNA is synthesized using the poly(A)RNA as a template and a reverse transcriptase. A recombinant DNA is obtained using in vitro recombinant DNA techniques by inserting the synthetic DNA into a vector DNA such as *Escherichia coli* plasmid DNA.

A process for producing the DNA and recombinant DNA of the present invention is explained in detail below.

The pituitary gland is excised from captured salmons and immediately freezed in a liquid nitrogen. Guanidinium thiocyanate is added to the freezed pituitary gland and the pituitary gland is disrupted and solubilized. Then, the solubilized pituitary gland is put on CsCl solution layer and subjected to ultra centrifugation to obtain whole cytoplasmic RNA as a precipitate. Alternatively, LiCl is added to the solubilized matter with guanidinium thiocyanate to recover only RNA as a precipitate.

The extracted RNA is dissolved in an NaCl or KCl hypertonic solution (for example, 0.5M) and passed through an oligo(dT) cellulose column to allow mRNA having polyadenylic acid [poly(A)] to be adsorbed on the column. Elution is carried out with water or a hypotonic salt solution such as 10 mM Tris-HCl buffer to isolate the mRNA having poly(A).

Synthesis of cDNA and insertion of the cDNA into a vector are carried out according to the method of Okayama-Berg [Okayama & Berg; Mol. Cell. Biol. 2, 161 (1982)] as follows.

First, a vector primer is synthesized. A vector, e.g. pCDV1, is treated with KpnI in an adequate solution such as a solution consisting of Tris-HCl buffer (e.g. pH 7.5, 10 mM), $MgCl_2$ (e.g. 6 mM) and NaCl (e.g. 10 mM) to cut pCDV1 at KpnI site. The DNA is incubated with terminal deoxynucleotidyltransferase at an appropriate temperature (e.g. 37° C.) for an appropriate period (e.g. 20 minutes) in a solution consisting of Tris-HCl buffer (e.g. pH 6.8, 30 mM), sodium cacodylate (e.g. 140 mM), $CoCl_2$ (e.g. 1 mM), dithiothreitol (e.g. 0.1 mM) and dTTP (e.g. 0.25 mM) to add about 60 thymidyl residues to the both 3' ends of the vector DNA. Then, the DNA is cut with EcoRI in a solution consisting of Tris-HCl buffer (e.g. pH 7.5, 10 mM), $MgCl_2$ (e.g. 6 mM) and NaCl (e.g. 100 mM). The digested solution is fractionated by low-gelling-temperature agarose gel electrophoresis (referred to as LGT method hereinafter) [Lars Wieslander: Analytical Biochemistry, 98, 305 (1979)] to recover a DNA fragment of about 3.1 Kb. Then, the DNA is dissolved in an NaCl or KCl hypertonic solution (e.g. 0.5M) and passed through a poly(dA) cellulose column to allow only vector primer molecules having poly(T) to be adsorbed on the column. Elution is carried out with water or a hypotonic salt solution such as 10 mM Tris-HCl buffer to isolate only the vector primer molecule with poly(T).

Then, a linker DNA is synthesized as follows. For example, pL1 DNA is treated with PstI in an appropriate solution such as a solution consisting of Tris-HCl buffer (e.g. pH 7.5, 10 mM), $MgCl_2$ (e.g. 6 mM) and NaCl (e.g. 50 mM) to cut pL1 at PstI site. The DNA is treated by the same mtehod as in the synthesis of the vector primer except that dGTP is added in place of dTTP, and about 15 oligo(dG) chains are added. The DNA is cut with HindIII in an appropriate solution such as a solution consisting of Tris-HCl buffer (e.g. pH 7.5, 10 mM), $MgCl_2$ (e.g. 6 mM) and NaCl (e.g. 60 mM). A DNA fragment of about 0.5 Kb is fractionated by agarose gel electrophoresis and recovered with DEAE paper. Thus, a linker DNA is obtained.

The thus obtained poly(A)RNA, vector primer and linker DNA are used to synthesize cDNA as follows. The poly(A)RNA and vector primer DNA are reacted with a reverse transcriptase at an appropriate temperature (e.g. 37° C.) for an appropriate period (e.g. 40 minutes) in a solution consisting of Tris-HCl buffer (e.g. pH 8.3, 50 mM), $MgCl_2$ (e.g. 8 mM), KCl (e.g. 30 mM), dithiothreitol (e.g. 0.3 mM), and dATP, dTTP, dCTP and dGTP (e.g. each 2 mM). About 15 oligo(dC) chains are added at the 3' ends of the thus obtained RNA-DNA double strand in the same conditions as in the case of the addition of (dT) chains to the vector primer except that dTTP is replaced with dCTP. The DNA is cut with HindIII in a solution consisting of Tris-HCl buffer (e.g. pH 7.5, 10 mM), $MgCl_2$ (e.g. 6 mM) and NaCl (e.g. 60 mM). The previously prepared linker DNA is mixed with the DNA and the mixture is incubated with *Escherichia coli* DNA ligase at an appropriate temperature (e.g. 12° C.) for an appropriate period (e.g. 16 hours) in a solution consisting of Tris-HCl buffer (e.g. pH 7.5, 20 mM), $MgCl_2$ (e.g. 4 mM), $(NH_4)_2SO_4$ (e.g. 10 mM), KCl (e.g. 0.1M) and β-nicotinamide adenine dinucleotide (β-NAD) (e.g. 0.1 mM) to prepare a ring of the cDNA and liner DNA. To the reaction solution is added 40 μM (final concentration) each dATP, dTTP, dGTP and dCTP. *Escherichia coli* DNA ligase, *Escherichia coli* DNA polymerase I and *Escherichia coli* ribonuclease H are added to replace the RNA part with DNA and to obtain a recombinant plasmid containing a complete double stranded cDNA.

An *Escherichia coli* strain, e.g. *Escherichia coli* c600SF8 is transformed with the thus obtained recombinant plasmid, for example, by the method of Scott, et al. [Katsuya Shigesada: Saibo Kogaku (Cell Engineering), 2, 616 (1983)]. Since an ampicillin resistance gene exists in the recombinant plasmid mentioned above, the *Escherichia coli* transformant is resistant to ampicillin.

Selection of a microorganism strain carrying a new recombinant plasmid DNA having a gene complementary to the mRNA of fish growth hormone from the ampicillin-resistant ($Ap^R$) strains is carried out as follows. That is, the transformants obtained above are fixed on a nitrocellulose filter and a synthetic DNA probe having a DNA sequence which is presumed from the amino acid sequence of a known salmon growth hormone polypeptide is hybridized thereto to select the transformant showing strong hybridization [the Method of Grunstein-Hogness, Proc. Natl. Acad. Sci., USA., 72, 3961 (1975)]. The probe DNA is synthesized by a conventional triester method [J. Am. Chem. Soc., 97, 7327 (1975)]. Selection by the synthesized DNA probe is more definitely carried out by the method of Southern, et al. [J. Mol. Biol., 98, 503 (1975)] and a recombinant plasmid having the gene complementary to a salmon growth hormone mRNA is identified by the same method mentioned above.

pSGH1 and pSGH14 are examples of the thus obtained recombinant plasmids. The plasmid can be used as a source of the DNA coding for salmon growth hormone.

Production of salmon growth hormone polypeptide by the expression of the DNA coding for salmon growth hormone in a microorganism:

The DNA coding for salmon growth hormone is cut out from the plasmid carrying the DNA and inserted into a vector DNA. The thus obtained recombinant DNA is incorporated in a microorganism and the thus obtained transformant is cultured to accumulate salmon growth hormone polypeptide in a medium. Then salmon growth hormone is recovered from the culture.

As the plasmid containing the DNA coding for salmon growth hormone, pSGH1 and pSGH14 mentioned above are preferable examples.

Figure 3:
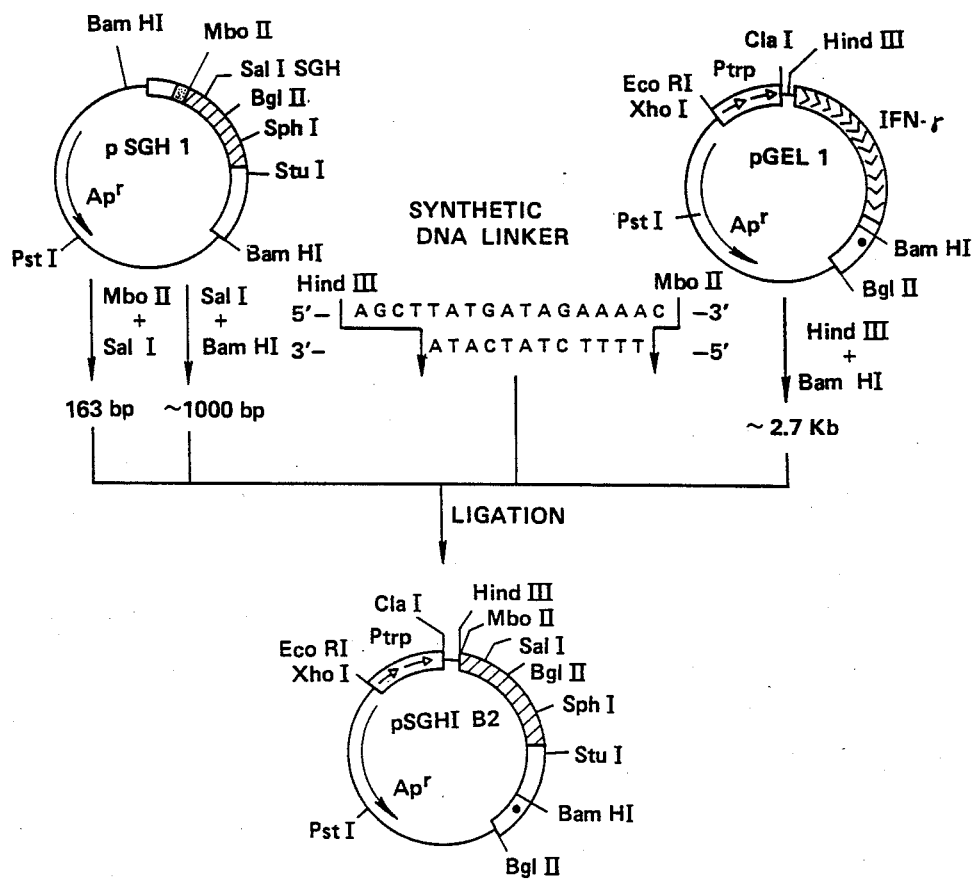
FIG. 3 is a flow sheet for constructing the recombinant plasmid pSGHIB2. Though many MboII sites are present in psGH1 and psGHIB2, only the sites necessary for the construction of the plasmid are referred to in FIG. 3.
Figure 4:
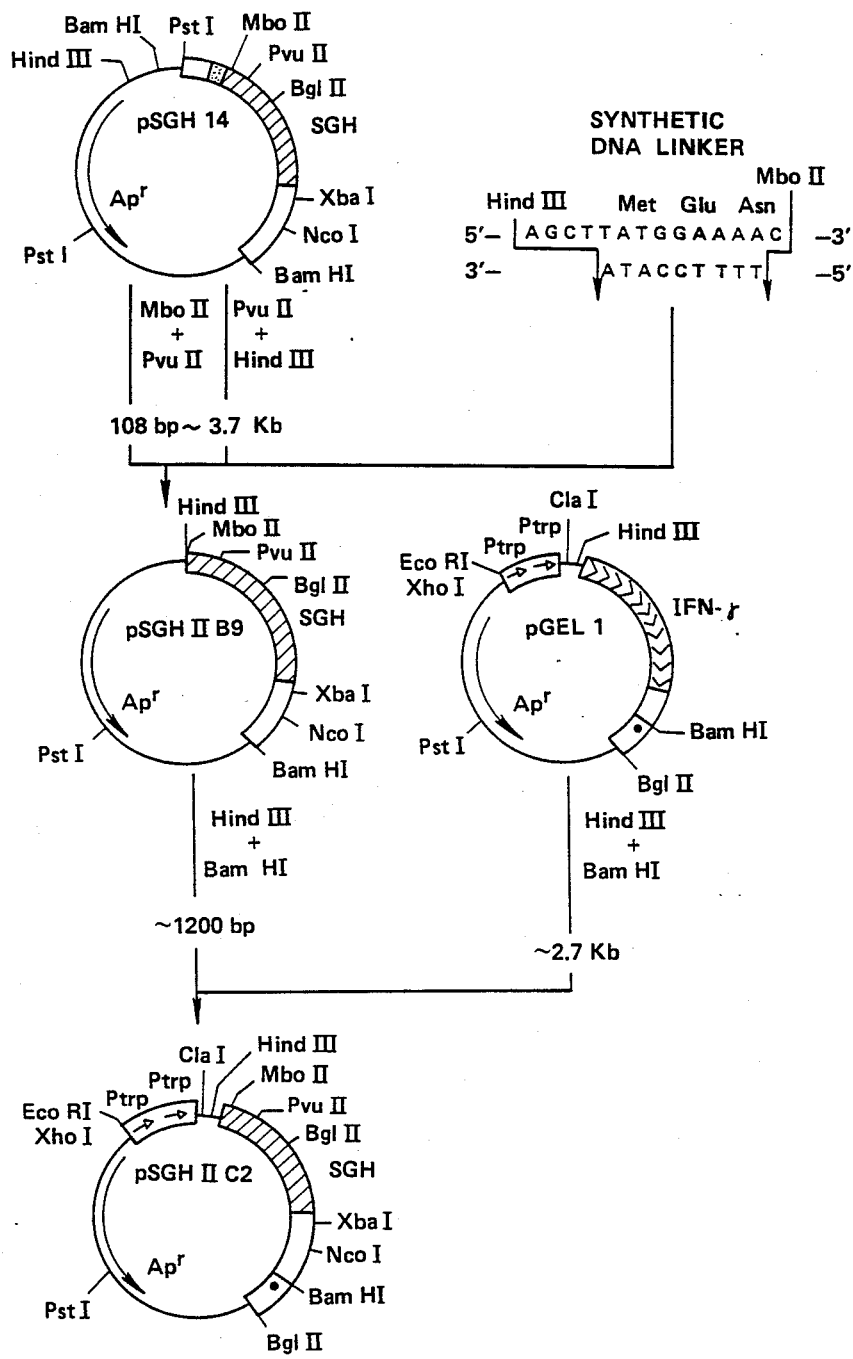
FIG. 4 is a flow sheet for constructing the recombinant plasmids pSGHIIB9 and pSGHIIC2.

As the vector DNA, any vector can be used so long as the DNA incorporated therein can be expressed in a microorganism. Preferably, a vector DNA wherein a foreign DNA can be inserted downstream from a suitable promoter such as trp promoter, lac promoter or $P_L$ promoter and the length between Shine-Dalgarno sequence (referred to as SD sequence hereinafter) and initiation codon (ATG) is adjusted, for example, to 6–18 base pairs is employed. Preferred example of vector DNA is plasmid pGEL1. pGEL1 is a plasmid as illustrated in FIG. 3 and FIG. 4 and a microorganism containing the plasmid was deposited with Fermentation Research Institute, Agency of Industrial Science and Technology (hereinafter referred to as FRI) as *Escherichia coli* IGEL1 under FERM BP-629 on OCT. 6, 1984. Recombination of the DNA coding for the polypeptide and the vector DNA can be carried out by a conventional recombinant DNA techniques wherein both DNAs are digested with restriction enzymes and religated with T4 DNA ligase.

In the case of pSGH1 and pGEL1, as illustrated in FIG. 3, MboII-SalI digestion fragment coding for salmon growth hormone and SalI-BamHI digestion fragment are separately prepared from psGH1 and HindIII-BamHI digestion fragment containing tryptophan promoter from pGEL1 is prepared. On the other hand, the synthetic DNA linker as set forth below is prepared.

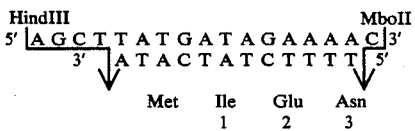

The DNA fragments and synthetic DNA liner described above are ligated with T4 DNA ligase to obtain the recombinant plasmid psGHIB2 as illustrated in FIG. 3. The plasmid codes for a mature salmon growth hormone.

In the case of psGH14 and pGEL1, as illustrated in FIG. 4, two step-construction is carried out. That is, MBoII-PvuII digestion fragment coding for the vicinity of the N-terminal of salmon growth hormone mature peptide and PvuII-HindIII digestion fragment containing the remained cDNA and the vector part are separately prepared from pSGH1. On the other hand, the synthetic DNA linker as set forth below is prepared.

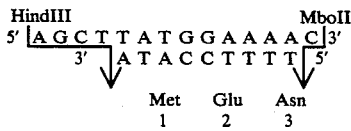

The DNA fragments and synthetic DNA liner described above are ligated with T4 DNA ligase to obtain the recombinant plasmid pSGHIIB9 as illustrated in FIG. 4. Then, HindIII-BamHI digestion fragment coding for the salmon growth hormone mature peptide is obtained from pSGHIIB9, and HindIII-BamHI digestion fragment containing tryptophan promoter is obtained from pGEL1. The two DNA fragments are ligated with T4 DNA ligase to obtain the recombinant plasmid pSGHIIC2 as illustrated in FIG. 4. The plasmid has a construction wherein a region coding for mature salmon growth hormone is ligated downstream from tryptophan promoter.

Reaction conditions required for the recombinant DNA techniques described above are generally as follows.

Digestion of the DNA with restriction enzymes is usually carried out by reacting with 0.1 to 20 μg of DNA with 0.1-100 units, preferably 1-3 units of restriction enzyme per 1 μg of DNA in a mixture of 2-200 mM, preferably 10-40 mM Tris-HCl (pH 6.0-9.5, preferably pH 7.0-8.0), 0-200 mM NaCl and 2-30 mM, preferably 5-10 mM MgCl₂ at 20°-50° C. (optimal temperature depends on restriction enzymes used) for 15 minutes to 24 hours. Reaction is usually stopped by heating at 55°-75° C. for 5-30 minutes, or alternatively by inactivating the restriction enzyme with a reagent such as phenol and diethylpyrocarbonate.

Purification of the DNA fragments formed by digestion with restriction enzymes is carried out by LGT method or polyacrlamide gel electrophoresis.

Ligation of the DNA fragments is carried out with 0.3-10 units of T4 DNA ligase in a mixture of 2-200 mM, preferably 10-40 mM Tris-HCl (pH 6.1-9.5, preferably 7.0-8.0), 2-20 mM, preferably 5-10 mM MgCl₂, 0.1-10 mM preferably 0.5-2.0 mM ATP and 1-50 mM, preferably 5-10 mM diethiothreitol at 1°-37° C., preferably 3+-20° C. for 15 minutes to 72 hours, preferably 2-20 hours.

The recombinant plasmid DNA formed by the ligation reaction is introduced into *Escherichia coli* by the transformation method of Cohen, et [S. N. Cohen, et al.: Proc. Natl, Acad. Sci. USA, 69, 2110 (1972)].

Isolation of the recombinant plasmid DNA from *Escherichia coli* carrying the DNA is carried out by the method described in Example 1 or the method of Birnboim, et al. [H. C. Birnboim, et al.: Nucleic Acids Res. 7, 1513 (1979)].

Plasmid DNA is digested with 1-10 kinds of restriction endonucleases and the cleavage sites are examined by agarose gel electrophoresis or polyacrylamide gel electrophoresis. Further, if necessary, the base sequence of the DNA is determined by the method of Maxam-Gilbert [Proc. Natl. Acad. Sci. 74, 560 (1977)] or the method of Sanger [Sanger, et al., Proc. Natl. Acad. Sci. USA, 74, 5463 (1977); Amersham Co., M13 cloning and sequencing handbook].

A recombinant plasmid DNA can be made as mentioned above.

The fish growth hormone polypeptide of the present invention is produced by the following method.

That is, *Escherichia coli* K-12 HB101 is transformed with a plasmid such as pSGHIB2 and pSGHIIC2 and an *Escherichia coli* strain carrying pSGHIB2 or pSGHIIC2 is selected from the ampicillin resistant colonies. The *Escherichia coli* strain carrying pSGHIB2 or pSGHIIC2 is cultured in a medium to produce the fish growth hormone polypeptide in the cultured cells.

As the medium, either a synthetic medium or a natural medium can be used so long as it is suitable for the growth of *Eschericia coli* and the production of the fish growth hormone polypeptide.

As a carbon source, glucose, fructose, lactose, glycerol, mannitol, sorbitol, etc. may be used.

As a nitrogen source, NH₄Cl, (NH₄)₂SO₄, casamino acid, yeast extract, polypeptone, meat extract, Bactotrypton, corn steep liquor, etc. may be used.

In addition, nutrients such as K₂HPO₄, KH₂PO₄, NaCl, MgSO₄, vitamine B₁ and MgCl₂ may be used.

Culturing is carried out at pH 5.5-8.5 and at 18°-40° C. with aeration and stirring.

After culturing for 5-90 hours, the salmon growth hormone polypeptide is accumulated in cultured cells. The collected cells are treated with lysozyme, disrupted by repeated freezing and thawing and subjected to centrifugation. The thus obtained supernatant fluid is subjected to extraction according to a conventional method for extraction of polypeptides to recover the polypeptide.

Detection of the polypeptide is carried out by heat-dissolving the cultured cells directly in Sample buffer of Laemmli [Laemmli, Nature, 227, 680 (1970)] by subjecting to SDS-polyacrylamide gel [the method of Laemmli: the reference mentioned above] and Coomassie Brilliant Blue staining.

Certain specific embodiments of the invention are illustrated by the following representative examples.

EXAMPLE 1

Preparation of poly(A)RNA from the pituitary gland of salmons

An RNA having poly(A) was prepared from the pituitary gland of salmons according to guanidinium thiocyanate-cesium chloride method [edited by Maniatis, et al. Molecular Cloning, p196, published by Cold Spring Harbor; Katsuya Shigesada, Saibo Kogaku (Cell Engineering), 2, 616 (1983)] as follows.

In this step, 2g of the freezed pituitary gland of salmons (corresponding to about 30 individuals) was disrupted and solubilized by Teflon homongenizer (5 rpm) in 10 ml of a solution consisting of 4M guanidinium thiocyanate, 0.5% sarcosine, 5 mM sodium citrate (pH 7) and 0.1M β-mercaptoethanol. The homogenate was passed through 18 G injector to cut the DNA and put on a layer of 1.2 ml each of 5.7M CsCl and 0.1M EDTA (pH 8) in an ultra centrifugation tube. Centrifugation was carried out at 35,000 rpm for 15 hours by Hitachi RPS40 rotor (product of Hitachi, Ltd.) to recover RNAs as a precipitate. The RNA precipitate was dissolved in 10 ml of Tris-HCl solution (pH 8.0) containing 1 mM EDTA. After extraction with phenol-chloroform, the RNA was recovered with ethanol as a precipitate. About 1 mg of the thus obtained RNA was dissolved in 1 ml of a solution consisting of 10 mM Tris-HCl (pH 8.0) and 1 mM EDTA. The solution was incubated at 65° C. for 5 minutes and 0.1 ml of 5M NaCl was added. The mixture was subjected to oligo(dT) cellulose column (product of P-L Biochemicals, column volume 0.5 ml) chromatography. The mRNA having poly(A) adsorbed on the column was eluted with a solution consisting of 10 mM Tris-HCl (pH 7.5) and 1 mM EDTA and fractionated by 0.2 ml portion to obtain about 10 μg of the mRNA having poly(A) in the 3rd to 5th fractions.

EXAMPLE 2

Synthesis of a cDNA and insertion of the cDNA into a vector

Synthesis of a cDNA and construction of a recombinant plasmid carrying the cDNA were carried out according to the method of Okayama-Berg [Mol. Cell. Biol., 2, 161 (1982)] as follows. The process is outlined in FIG. 1.

In this step, 400 μg of pCDV1 [Okayama & Berg: Mol. Cell. Biol., 3, 280 (1983)] was added to 300 μl of a solution consisting of 10 mM Tris-HCl (pH 7.5), 6 mM MgCl$_2$ and 10 mM NaCl, and further 500 units of KpnI (product of Takara Shuzo Co. the restriction enzymes used hereinafter are all products of Takara Shuzo Co., unless otherwise specified) was added. Reaction was carried out at 37° C. for 6 hours to cut the plasmid at KpnI site. After phenol-chloroform extraction, a DNA was recovered by ethanol precipitation. About 200 μg of the DNA cut with KpnI was added to 200 μl of a solution prepared by adding 0.25 mM dTTP to a buffer (referred to as TdT buffer hereinafter) consisting of 40 mM sodium cacodylate, 30 mM Tris-HCl (pH 6.8), 1 mM CaCl$_2$ and 0.1 mM dithiothreitol (referred to as DTT hereinafter). Further, 81 units of terminal deoxynucleotidyl transferase (referred to as TdT hereinafter) (product of P-L Biochemicals) was added and reaction was carried out at 37° C. for 11 minutes. Thereby, about 67 poly(dT) chains were added at 3′ ends of pCDV1 cleaved with KpnI. About 100 μg of pCDV1 DNA associated with poly(dT) chains was recovered from the solution by phenol-chloroform extraction and ethanol precipitation. The DNA was added to 150 μl of a buffer consisting of 10 mM Tris-HCl (pH 7.5), 6 mM MgCl$_2$ and 100 mM NaCl. Further, 360 units of EcoRI was added and reaction was carried out at 37° C. for 2 hours. The reaction product was subjected to LGT method to obtain a DNA fragment of about 3.1 Kb which is about 60 μg of pCDV1 with poly(dT) chains. The DNA was dissolved in 500 μl of a solution consisting of 10 mM Tris-HCl (pH 8.0) and 1 mM EDTA. The solution was incubated at 65° C. for 5 minutes and 50 μl of 5M NaCl was added under ice cooling. The mixture was subjected to oligo(dA) cellulose column (product of Collaborative Research) chromatography. The DNA with enough poly(dT) chains was absorbed on the column. Elution was carried out with a solution consisting of 10 mM Tris-HCl (pH 8.0) and 1 mM EDTA to obtain 27 μg of pCDV1 with poly(dT) chains (referred to as vector primer hereinafter).

Then, a linker DNA was prepared as follows.

About 14 μg of pL1 [Okayamo & Berg: Mol. Cell. Biol., 3, 280 (1983)] was added to 200 μl of a buffer consisting of 10 mM Tris-HCl (pH 7.5), 6 mM MgCl$_2$ and 50 mM NaCl. Further, 50 units of PstI was added and reaction was carried out at 37° C. for 4 hours to cut pL1 DNA at PstI site. The reaction product was subjected to phenol-chloroform extraction and ethanol precipitation to recover about 13 μg of pL1 DNA cut at PstI site. About 13 μg of the DNA was added to 50 μl of TdT buffer containing 0.25 mM (final concentration) dGTP. Further, 54 units of TdT (product of P-L Biochemicals) was added and incubation was carried out at 37° C. for 13 minutes to add about 14 (dG) chains at the 3′ ends of pL1 cut with PstI. A DNA was recovered by phenol-chloroform extraction and ethanol precipitation. The DNA was added to 100 μl of a buffer consisting of 10 mM Tris-HCl (pH 7.5), 6 mM MgCl$_2$ and 60 mM NaCl. Further, 80 units of HindIII was added and incubation was carried out at 37° C. for 3 hours to cut pL1 DNA at HindIII site. The reaction product was fractionated by agarose gel electrophoresis and a DNA fragment of about 0.5 Kb was recovered by DEAE paper method [Dretzen, et al., Anal. Biochem., 112, 295 (1981)]. The DNA was linker DNA with oligo (dG) chain (referred to as linker-DNA hereinafter).

About 2 μg of poly(A)RNA and about 1.4 μg of vector primer prepared above were dissolved in 22.3 μl of a solution consisting of 50 mM Tris-HCl (pH 8.3), 8 mM MgCl$_2$, 30 mM KCl, 0.3 mM DTT, 2 mM dNTP (dATP, dTTP, dGTP and dCTP) and 10 units of ribonuclease inhibitor (product of P-L Biochemicals). Ten units of reverse transcriptase (product of Seikagaku Kogyo Co.) was added and incubation was carried out at 37° C. for 40 minutes to synthesize a DNA complementary to mRNA. The reaction product was subjected to phenol-chloroform extraction and ethanol precipitation to recover a vector-primer DNA associated with RNA-DNA double strand. The DNA was dissolved in 20 μl of TdT buffer containing 66 μM dCTP and 0.2 μg of poly(A). Fourteen units of TdT (product of P-L Biochemicals) was added and incubation was carried out at 37° C. for 8 minutes to add 12 (dC) chains at the 3' end of the cDNA. The reaction product was subjected to phenol-chloroform extraction and ethanol precipitation to recover a cDNA-vector primer DNA associated with (dC) chains. The DNA was dissolved in 400 μl of a solution consisting of 10 mM Tris-HCl (pH 7.5), 6 mM $MgCl_2$ and 60 mM NaCl. Twenty units of HindIII was added and incubation was carried out at 37° C. for 2 hours to cut the DNA at HindIII site. The reaction product was subjected to phenol-chloroform extraction and ethanol precipitation to obtain 0.5 pmole of a cDNA-vector primer DNA associated with (dC) chains. Then, 0.08 pmole of the DNA and 0.16 pmole of the linker-DNA mentioned above were added to 40 μl of a solution consisting of 10 mM Tris-HCl (pH 7.5), 0.1M NaCl and 1 mM EDTA and incubations were carried out at 65° C., 42° C. and 0° C. for 10 minutes, 25 minutes and 30 minutes, respectively. The reaction solution was adjusted to 400 μl (total volume) of a solution having a composition of 20 mM Tris-HCl (pH 7.5), 4 mM $MgCl_2$, 10 mM $(NH_4)_2SO_4$, 0.1M KCl and 0.1 mM β-NAD. Ten units of *Eschericia coli* DNA ligase (product of New England Biolabs) was added to the reaction solution and incubation was carried out at 11° C. overnight. The reaction solution was adjusted to a solution containing 40 μM dNTP and 0.15 mM β-NAD. Five units of *Eschericia coli* DNA ligase, 7 units of *Escherichia coli* DNA polymerase I (product of P-L Biochemicals) and 2 units of *Escherichia coli* ribonuclease H (product of P-L Biochemicals) were added and incubation was carried out at 12° C. for one hour and successively at 25° for one hour. By the reaction mentioned above, a recombinant DNA containing cDNA was cyclized, the RNA part of the RNA-DNA double strand was replaced with DNA and a recombinant plasmid having complete double stranded DNA was formed.

EXAMPLE 3

Selection of a recombinant DNA containing a salmon growth hormone cDNA

*Escherichia coli* c600SF8 [Cameron: Proc. Natl. Acad. Sci. USA, 72, 3416 (1975)] was transformed using the recombinant plasmid obtained in Example 2 by the method of Scott, et al. [Katsuya Shigesada: Saibo Kogaku (Cell Engineering) 2, 616 (1983)]. Among about 10,000 colonies thus obtained, 4,800 colonies were fixed on nitrocellulose. Eight strains were selected which hybridized strong at 40° C. with the probe wherein a synthetic DNA corresponding to the 23rd to 28th amino acid sequence from the N-terminal of the salmon growth hormone, i.e.

```
         1 2 3 4 5 6 7 8 9 10 11 12 13 14 15 16 17
      5'-A A A A T G T T T A  A  C  G  A  C  T  T
                (G)       (C)    (T)   (T)
```

(the 3rd base is A or G, the 9th is T or C, the 12th is C or T, the 15th is C or T and combination of the bases makes 16 kinds of synthetic DNAs) is labelled with $^{32}P$ [the method of Grunstein-Hogness, Proc. Natl. Acad. Sci., USA, 72, 3961 (1975)]. It was confirmed by the method of Southern [J. Mol. Biol., 98, 503 (1975)] that the 8 strains hybridized with the probe mentioned above and the synthetic DNA probe corresponding to the amino acid sequence around C-terminal

```
         1 2 3 4 5 6 7 8 9 10 11 12 13 14
      5'-C A C A A A G T A G  A  G  A  C
            (T)   (G)  (T)      (A)
                       (G)
                       (C)
```

(the 3rd base is C or T, the 6th is A or G, the 9th is A, T, G or C, the 12th is G or A and combination of the bases makes 32 kinds of synthetic DNAs). The plasmids named pSGH 1, 3, 6, 8, 9, 10, 14 and 17 respectively have the DNA sequence presumed from the amino acid sequence of the known salmon growth hormone and are considered to contain a growth hormone cDNA.

EXAMPLE 4

The base sequence of plasmids pSGH1 and pSGH14

Figure 2:
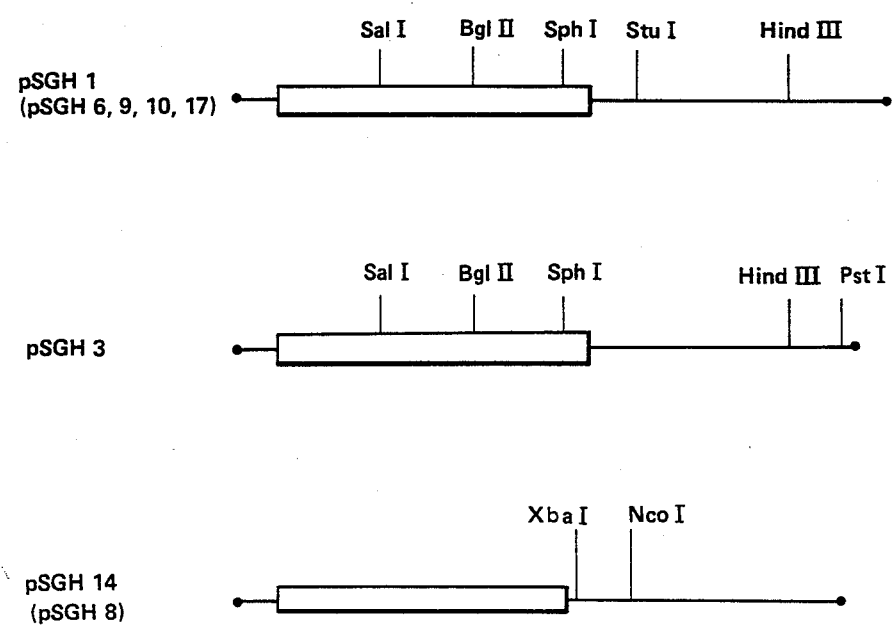
FIG. 2 illustrates the restriction enzyme maps of the cDNA in pSGH1, psGH3 and psGH14.

The 8 plasmids obtained above were digested with various restriction endonucleases and cleavage maps of the cDNA parts were determined. The plasmids were classified into three groups, i.e. the group of pSGH 1, 6, 9, 10 and 17, the group of pSGH3 and the group of pSGH8 and 14 from the positions of restriction endonuclease sites. The restriction endonuclease maps of each group are illustrated in FIG. 2.

The whole nucleotide sequence of the translation region of the plasmids which hybridized most strongly with the synthetic DNA probe as performed in Example 3 and are considered to contain almost complete cDNA, especially pSGH1 was determined by the method of Sanger using M13 phage [Sanger, et al., Proc. Natl. Acad. Sci., USA, 74, 5463 (1977): Amersham, M13 cloning and sequencing handbook]. The sequence is illustrated in Table 1. In Table 1, the base numbers 1–66 code for signal peptide and 67–630 code for the mature salmon growth hormone polypeptide.

Further, among pSGH8 and pSGH14 which differ from the pSGH1-including group in restriction sites, pSGH14 which is considered to contain the cDNA which is longer and has an almost complete length is subjected to the method of Sanger using M13 phage.

Genetic Code [Universal]

```
                10              20             30
           ATGGGACAAGTGTTTCTGCTGATGCCAGTC
           MetGlyGlnValPheLeuLeuMetProVal 40              50             60
           TTACTGGTCAGTTGTTTCCTGAGTCAAGGG
           LeuLeuValSerCysPheLeuSerGlnGly 70              80             90
           GCAGCGATAGAAAACCAACGGCTCTTCAAC
           AlaAlaIleGluAsnGlnArgLeuPheAsn 100             110            120
           ATCGCGGTCAGTCGGGTGCAACATCTCCAC
           IleAlaValSerArgValGlnHisLeuHis 130             140            150
           CTATTGGCTCAGAAAATGTTCAATGACTTT
           LeuLeuAlaGlnLysMetPheAsnAspPhe 160             170            180
           GACGGTACCCTGTTGCCTGATGAACGCAGA
           AspGlyThrLeuLeuProAspGluArgArg 190             200            210
           CAGCTGAACAAGATATTCCTGCTGGACTTC
           GlnLeuAsnLysIlePheLeuLeuAspPhe
```

-continued
Genetic Code [Universal]

```
        220         230         240
TGTAACTCTGACTCCATCGTGAGCCCAGTC
CysAsnSerAspSerIleValSerProVal 250         260         270
GACAAGCAGGAGACTCAGAAGAGTTCAGTC
AspLysGlnGluThrGlnLysSerSerVal 280         290         300
CTGAAGCTGCTCCACATTTCTTTCCGTCTG
LeuLysLeuLeuHisIleSerPheArgLeu 310         320         330
ATTGAATCCTGGGAGTACCCTAGCCAGACC
IleGluSerTrpGluTyrProSerGlnThr 340         350         360
CTGACCATCTCCAACAGCCTAATGGTCAGA
LeuThrIleSerAsnSerLeuMetValArg 370         380         390
AACTCCAACCAGATCTCTGAGAAGCTCAGC
AsnSerAsnGlnIleSerGluLysLeuSer 400         410         420
GACTCTAAAGTGGGCATCAACCTGCTCATC
AspLeuLysValGlyIleAsnLeuLeuIle 430         440         450
GAGGGGAGCCAGGAAGGGGTACTGAGCCTG
GluGlySerGlnGluGlyValLeuSerLeu 460         470         480
GATGACAATGACTCTCAGCATCTGCCCCCC
AspAspAsnAspSerGlnHisLeuProPro 490         500         510
TACGGGAACTACTACCAGAACCTGGGGGGC
TyrGlyAsnTyrTyrGlnAsnLeuGlyGly 520         530         540
GACGGAAACGTCAGGAGGAACTACGAGTTG
AspGlyAsnValArgArgAsnTyrGluLeu 550         560         570
TTGGCATGCTTCAAGAAGGACATGCACAAG
LeuAlaCysPheLysLysAspMetHisLys 580         590         600
GTCGAGACCTACCTGACCGTCGCCAAGTGC
ValGluThrTyrLeuThrValAlaLysCys 610         620         630
AGGAAGTCACTGGAGGCCAACTGCACTCTGTAG
ArgLysSerLeuGluAlaAsnCysThrLeu***
```

Genetic Code [Universal]

```
        10          20          30
ATGGGACAAGTGTTTCTGCTGATGCCAGTC
MetGlyGlnValPheLeuLeuMetProVal 40          50          60
TTACTGGTCAGTTGTTTCCTGAGTCAAGGG
LeuLeuValSerCysPheLeuSerGlnGly 70          80          90
GCGGCGATGGAAAACCAACGGCTCTTCAAC
MetAlaMetGluAsnGlnArgLeuPheAsn 100         110         120
ATCGTGGTCAACCGGGTGCAACACCTCCAC
IleValValAsnArgValGlnHisLeuHis 130         140         150
CTATTGGCTCAGAAAATGTTCAACGACTTT
LeuLeuAlaGlnLysMetPheAsnAspPhe
```

-continued
Genetic Code [Universal]

```
        160         170         180
GAAGGCACCCTGTTGTCTGATGAACGCAGA
GluGlyThrLeuLeuSerAspGluArgArg 190         200         210
CAGCTGAACAAGATATTCCTGCTGGACTTC
GlnLeuAsnLysIlePheLeuLeuAspPhe 220         230         240
TGTAACTCTGACTCCATCGTGAGCCCCATC
CysAsnSerAspSerIleValSerProIle 250         260         270
GACAAGCACGAGACTCAGAAGAGTTCAGTC
AspLysGlnGluThrGlnLysSerSerVal 280         290         300
CTGAAGCTGCTCCATATCTCTTTCCGCCTG
LeuLysLeuLeuHisIleSerPheArgLeu 310         320         330
ATTGAATCCTGGGAGTACCCTAGCCAGACC
IleGluSerTrpGluTyrProSerGlnThr 340         350         360
CTGACCATCTCCAACAGCCTAATGGTCAGA
LeuThrIleSerAsnSerLeuMetValArg 370         380         390
AACTCCAACCAGATCTCTGAGAAGCTCAGC
AsnSerAsnGlnIleSerGluLysLeuSer 400         410         420
GACTCTAAAGTGGGCATCAACCTGCTCATC
AspLeuLysValGlyIleAsnLeuLeuIle 430         440         450
GAGGGGAGCCAGGAAGGGGTACTGAGCCTG
GluGlySerGlnGluGlyValLeuSerLeu 460         470         480
GATGACAATGACTCTCAGCATCTGCCCCCC
AspAspAsnAspSerGlnHisLeuProPro 490         500         510
TACGGGAACTACTACCAGAACCTGGGGGGC
TyrGlyAsnTyrTyrGlnAsnLeuGlyGly 520         530         540
GACGGCAACGTCAGGAGGAACTACGAACTG
AspGlyAsnValArgArgAsnTyrGluLeu 550         560         570
TTGGCCTGCTTCAAGAAGGACATGCATAAG
LeuAlaCysPheLysLysAspMetHisLys 580         590         600
GTTGAGACCTACCTGACCGTCGCTAAGTGC
ValGluThrTyrLeuThrValAlaLysCys 610         620         630
AGGAAGTCACTGGAGGCCAACTGCACTCTGTAA
ArgLysSerLeuGluAlaAsnCysThrLeu***
```

In Table 2, the base numbers 1-66 code for signal peptide and 67-630 code for the mature salmon growth hormone polypeptide.

The polypeptide encoded by the cDNA completely coincides with the polypeptide encoded by pSGH1 in 22 amino acids of the signal peptide but differs in 12 amino acids of the mature peptide in 188 amino acids as illustrated in Table 2 by underlines. Further, so long as the N-terminal 40 amino acid sequence determined from the salmon growth hormone polypeptide is referred to, 5 amino acids are clearly different. Therefore, it is considered that the cDNA contained in pSGH14 codes for a fish growth hormone differing from pSGH1. *Escherichia coli* containing pSGH1 and pSGH14 were deposited with the FRI as *Escherichia coli* ESGH1 (FERM BP-551) and ESGH14 (FERM BP-611) on June 23, 1984 and Sept. 20, 1984, respectively.

EXAMPLE 5

Construction of recombinant plasmid pSGHIB2 coding for the mature salmon growth hormone polypeptide In this example, 5 μg of plasmid pSGH1 containing a DNA coding for the salmon growth hormone polypeptide was dissolved in 40 μl of a solution containing 20 mM Tris-HCl (pH 7.5), 10 mM MgCl₂, and 10 mM NaCl (referred to as "Y-10 buffer solution" hereinafter). Then, 10 units of restriction enzyme MboII (product of New England Biolabs Co.) was added and digestion reaction was carried out at 37° C. for 3 hours. The concentration of NaCl in the solution was adjusted to 175 mM and 10 units of SalI was added. Digestion reaction was carried out at 37° C. for 3 hours. About 0.2 μg of DNA fragment of 163 bp corresponding to N-terminal region was obtained from the reaction solution by LGT method.

Then, 5 μg of pSGH1 was dissolved in 40 μl of a solution consisting of 20 mM Tris-HCl (pH 7.5), 10 mM MgCl₂ and 100 mM NaCl (referred to as "Y-100 buffer solution" hereinafter). Ten units of BamHI was added and digestion reaction was carried out at 37° C. for 3 hours. Then, the concentration of NaCl in the reaction solution was adjusted to 175 mM and 10 units of SalI was added. Digestion reaction was carried out at 37° C. for 3 hours. About 0.5 μg of a DNA fragment of about 900 bp containing C-terminal region and 3'-non-translational region was obtained from the reaction solution by LGT method.

Separately, 5 μg of pGEL1 was dissolved in 40 μl of Y-100 buffer solution and 10 units each of BamHI and HindIII were added. Digestion reaction was carried out at 30° C. for 3 hours. About 1 82 g of a DNA fragment of 2.7 Kb containing a tryptophan promoter was obtained from the reaction solution.

In order to add a translational initiation codon ATG necessary for the expression of the DNA coding for the mature salmon growth hormone polypeptide and to ligate a vector DNA and the DNA mentioned above, a DNA linker as set forth below was synthesized.

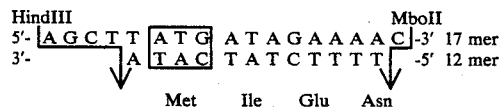

Two single chain DNAs of 17-mer and 12-mer were synthesized by a conventional triester method [R. Crea, et al.: Proc. Natl. Acad. Sci., 75, 5765 (1978)]. Then, 12 pmole each of the 17-mer and 12-mer DNAs were dissolved in 20 μl of a solution consisting of 50 mM Tris-HCl (pH 7.5), 10 mM MgCl₂, 10 mM dithiothreitol, and 1 mM ATP. Six units of T4 polynucleotide kinase (product of Takara Shuzo Co.) was added and phosphorylation reaction was carried out at 37° C. for 60 minutes.

Then, 0.1 pmole of MboII-SalI fragment (163 bp) of pSGH1, 0.06 pmole of SalI-BamHI fragment (about 900 bp) of pSGH1 and 0.02 pmole of HindIII-BamHI fragment (about 2.7 Kb) of pGEL1 obtained above were dissolved in 30 μl of a solution consisting of 50 mM Tris-HCl (pH 7.5), 10 mM MgCl₂, 10 mM dithiothreitol and 1 mM ATP. Five μl of the synthetic DNA phosphorylation reaction solution obtained above was added. Six units of T4 DNA ligase (product of Takara Shuzo Co.) was added to the mixture and ligation reaction was carried out at 4° C. for 18 hours.

*Escherichia coli* HB101 [Bolivar, et al., Gene, 2, 75 (1977)] was transformed using the reaction solution to obtain an Apᴿ colony. A plasmid DNA pSGHIB2 as illustrated in FIG. 3 was recovered from the colony. The structure of pSGHIB2 was recognized by the cleavage with EcoRI, HindIII, ClaI, BglII, SalI and BamHI and agarose gel electrophoresis. The sequence of the DNA coding for N-terminal region of the salmon growth hormone polypeptide in pSGHIB2 was determined according to the method of Sanger [Sanger, et al.: Proc. Natl. Acad. Sci. USA, 74, 5463 (1977); Amersham Co., M13 cloning and sequencing handbook] using M13 phage and illustrated below.

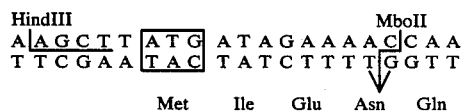

As the result, it was confirmed that pSGHIB2 contains the DNA coding for the mature salmon growth hormone polypeptide. *Escherichia coli* containing plasmid pSGHIB2 was deposited with the FRI as *Escherichia coli* ESGHIB2 under FERM BP-612 on Sept. 20, 1984.

EXAMPLE 6

(1) Construction of recombinant plasmid pSGHIIB9 coding for the mature salmon growth hormone polypeptide from pSGH14

In this example, 5 μg of plasmid pSGH14 containing a DNA coding for a salmon growth hormone polypeptide was dissolved in 100 μl of a solution containing 20 mM Tris-HCl (pH 7.5), 10 mM MgCl₂, and 10 mM NaCl. Then, 10 units of restriction enzyme MboII (product of New England Biolabs Co.) was added and digestion reaction was carried out at 37° C. for 3 hours. The concentration of NaCl in the solution was adjusted to 50 mM and 10 units of PvuII was added. Digestion reaction was carried out at 37° C. for 3 hours. About 0.05 μg of DNA fragment of 108 bp corresponding to N-terminal region was obtained from the reaction solution by polyacrylamide gel electrophoresis and DEAE paper method.

Then, 5 μg of pSGH14 was dissolved in 40 μl of a solution consisting of 20 mM Tris-HCl (pH 7.5), 10 mM MgCl₂ and 50 mM NaCl (referred to as "Y-50 buffer solution" hereinafter). Ten units each of PvuII and HindIII were added and digestion reaction was carried out at 37+ C. for 3 hours. About 0.5 μg of a DNA fragment of about 3.3 Kb containing C terminal region and 3'-non-transitional region of the growth hormone derived from pSGH14 and a part of the vector was obtained from the reaction solution by LGT method.

In order to add a translational initiation codon ATG necessary for the expression of the DNA coding for the mature salmon growth hormone polypeptide and to ligate a vector DNA and the DNA mentioned above, a DNA linker as set forth below was synthesized.

Met Glu Asn

Two single chain DNAs of 14-mer and 9-mer were synthesized by a conventional triester method [R. Crea, et al.: Proc. Natl. Acad. Sci., USA, 75, 5765 (1978)]. Then, 39 pmole each of the 14-mer and 9-mer DNAs were dissolved in 20 μl of a solution consisting of 50 mM Tris-HCl (pH 7.5), 10 mM $MgCl_2$, 10 mM dithiothreitol, and 1 mM ATP. Six units of T4 polynucleotide kinase (product of Takara Shuzo Co.) was added and phosphorylation reaction was carried out at 37° C. for 60 minutes.

Then, 0.08 pmole of MboII-PvuII fragment (108 bp) of pSGH14 and 0.02 pmole of PvuII-HindIII fragment (about 3.7 Kb) of pSGH14 obtained above were dissolved in 30 μl of a solution consisting of 50 mM Tris-HCl (pH 7.5), 10 mM $MgCl_2$, 10 mM dithiothreitol and 1 mM ATP. Five μl of the synthetic DNA phosphorylation reaction solution obtained above was added. Six units of T4 DNA ligase was added to the mixture and ligation reaction was carried out at 4° C. for 18 hours.

*Escherichia coli* HB101 [Bolivar, et al., Gene, 2, 75 (1977)] was transformed using the reaction solution to obtain an $Ap^R$ colony. A plasmid DNA pSGHIIB9 as illustrated in FIG. 4 was recovered from the colony. The structure of pSGHIIB9 was recognized by the cleavage with HindIII, XbaI, BglII, and BamHI and agarose gel electrophoresis.

(2) Insertion of a region coding for the mature salmon growth hormone polypeptide in pSGHIIB9 into an expresion vector pGEL1

In this step, 5 μg of pSGHIIB9 was dissolved in 40 μl of Y-50 buffer solution and 10 units each of BamHI and HindIII were added. Digestion reaction was carried out at 37° C. for 3 hours. About 0.1 μg of a DNA fragment of about 1200 bp coding for the whole mature salmon growth hormone polypeptide was obtained from the reaction solution by LGT method.

Separately, 5 μg of pGEL1 was dissolved in 40 μl of Y-50 buffer solution and 10 units each of BamHI and HindIII were added. Digestion reaction was carried out at 37° C. for 3 hours. About 0.1 μg of a DNA fragment of about 2.7 Kb containing a tryptophan promoter was obtained from the reaction solution by LGT method.

Then, 0.01 μg of HindIII-BamHI fragment (about 1200 bp) of pSGHIIB9 and 0.015 μg of HindIII-BamHI fragment (about 2.7 Kb) of pGEL1 were dissolved in 30 μl of a solution consisting of 50 mM Tris-HCl (pH 7.5), 10 mM $MgCl_2$, 10 mM dithiothreitol and 1 mM ATP and 6 units of T4 DNA ligase was added. Ligation reaction was carried out at 4° C. for 18 hours.

*Escherichia coli* HB101 was transformed using the reaction solution to obtain an $Ap^R$ colony. A plasmid DNA pSGHIIC2 as illustrated in FIG. 4 was recovered from the colony. The structure of pSGHIIC2 was recognized by the cleavage with EcoRI, HindIII, ClaI, BglII and BamHI and agarose gel electrophoresis.

*Escherichia coli* strains containing plasmids pSGHIIB9 and pSGHIIC2 were deposited with the FRI as *Escherichia coli* ESGHIIB9 and ESGHIIC2 under FERM BP-707 and 708, respectively on Feb. 8, 1985.

EXAMPLE 7

Production of the novel salmon growth hormone polypeptide by *Escherichia coli* containing pSGHIB2 or pSGHIIC2

*Escherichia coli* W3110 (FERM BP-732) was transformed with the recombinant plasmid pSGHIB2 or pSGHIIC2 obtained in Example 5 or Example 6 by a conventional method. An $Ap^R$ colony obtained was inoculated in 8 ml of MCG medium (pH 7.2) consisting of 0.6% $Na_2HPO_4$, 0.3% $KH_2PO_4$, 0.5% NaCl, 0.1% $NH_4Cl$, 0.5% glucose, 0.5% casamino acid, 1 mM $MgSO_4$ and 4 μg/ml vitamine B1 and culturing was carried out at 30° C. for 18 hours. The culture broth was centrifuged at 8,000 rpm for 10 minutes to recover cells. The cells were suspended in the sample buffer of Laemmli and subjected to SDS-polyacrylamide gel electrophoresis and Coomassie Brilliant Blue staining to detect a polypeptide band at the portion of a molecular weight of about 25,000. The band was not observed in the case of using *Escherichia coli* which does not contain the plasmid. As the result, it was confirmed that *Escherichia coli* carrying pSGHIB2 or pSGHIIC2 produced the salmon growth hormone polypeptide in a large amount.

What is claimed is:

1. A DNA consisting essentially of a DNA coding for a fish growth hormone polypeptide having the peptide sequence:

```
          10         20         30
ATGGGACAAGTGTTTCTGCTGATGCCAGTC
MetGlyGlnValPheLeuLeuMetProVal 40         50         60
TTACTGGTCAGTTGTTTCCTGAGTCAAGGG
LeuLeuValSerCysPheLeuSerGlnGly 70         80         90
GCAGCGATAGAAAACCAACGGCTCTTCAAC
AlaAlaIleGluAsnGlnArgLeuPheAsn 100        110        120
ATCGCGGTCAGTCGGGTGCAACATCTCCAC
IleAlaValSerArgValGlnHisLeuHis 130        140        150
CTATTGGCTCAGAAAATGTTCAATGACTTT
LeuLeuAlaGlnLysMetPheAsnAspPhe 160        170        180
GACGGTACCCTGTTGCCTGATGAACGCAGA
AspGlyThrLeuLeuProAspGluArgArg 190        200        210
CAGCTGAACAAGATATTCCTGCTGGACTTC
GlnLeuAsnLysIlePheLeuLeuAspPhe 220        230        240
TGTAACTCTGACTCCATCGTGAGCCCAGTC
CysAsnSerAspSerIleValSerProVal 250        260        270
GACAAGCAGGAGACTCAGAAGAGTTCAGTC
AspLysGlnGluThrGlnLysSerSerVal 280        290        300
CTGAAGCTGCTCCACATTTCTTTCCGTCTG
LeuLysLeuLeuHisIleSerPheArgLeu 310        320        330
ATTGAATCCTGGGAGTACCCTAGCCAGACC
IleGluSerTrpGluTyrProSerGlnThr
```

-continued

```
             340       350       360
       CTGACCATCTCCAACAGCCTAATGGTCAGA
       LeuThrIleSerAsnSerLeuMetValArg 370       380       390
       AACTCCAACCAGATCTCTGAGAAGCTCAGC
       AsnSerAsnGlnIleSerGluLysLeuSer 400       410       420
       GACTCTAAAGTGGGCATCAACCTGCTCATC
       AspLeuLysValGlyIleAsnLeuLeuIle 430       440       450
       GAGGGGAGCCAGGAAGGGGTACTGAGCCTG
       GluGlySerGlnGluGlyValLeuSerLeu 460       470       480
       GATGACAATGACTCTCAGCATCTGCCCCCC
       AspAspAsnAspSerGlnHisLeuProPro 490       500       510
       TACGGGAACTACTACCAGAACCTGGGGGGC
       TyrGlyAsnTyrTyrGlnAsnLeuGlyGly 520       530       540
       GACGGAAACGTCAGGAGGAACTACGAGTTG
       AspGlyAsnValArgArgAsnTyrGluLeu 550       560       570
       TTGGCATGCTTCAAGAAGGACATGCACAAG
       LeuAlaCysPheLysLysAspMetHisLys 580       590       600
       GTCGAGACCTACCTGACCGTCGCCAAGTGC
       ValGluThrTyrLeuThrValAlaLysCys 610       620       630
       AGGAAGTCACTGGAGGCCAACTGCACTCTGTAG
       ArgLysSerLeuGluAlaAsnCysThrLeu***
``` or

```
       10        20        30
ATGGGACAAGTGTTTCTGCTGATGCCAGTC
MetGlyGlnValPheLeuLeuMetProVal 40        50        60
       TTACTGGTCAGTTGTTTCCTGAGTCAAGGG
       LeuLeuValSerCysPheLeuSerGlnGly 70        80        90
       GCGGCGATGGAAAAACCAACGGCTCTTCAAC
       MetAlaMetGluAsnGlnArgLeuPheAsn 100       110       120
       ATCGTGGTCAACCGGGTGCAACACCTCCAC
       IleValValAsnArgValGlnHisLeuHis 130       140       150
       CTATTGGCTCAGAAAATGTTCAACGACTTT
       LeuLeuAlaGlnLysMetPheAsnAspPhe 160       170       180
       GAAGGCACCCTGTTGTCTGATGAACGAGA
       GluGlyThrLeuLeuSerAspGluArgArg 190       200       210
       CAGCTGAACAAGATATTCCTGCTGGACTTC
       GlnLeuAsnLysIlePheLeuLeuAspPhe 220       230       240
       TGTAACTCTGACTCCATCGTGAGCCCCATC
       CysAsnSerAspSerIleValSerProIle 250       260       270
       GACAAGCACGAGACTCAGAAGAGTTCAGTC
       AspLysGlnGluThrGlnLysSerSerVal 280       290       300
       CTGAAGCTGCTCCATATCTCTTTCCGCCTG
       LeuLysLeuLeuHisIleSerPheArgLeu
```

-continued

```
             310       320       330
       ATTGAATCCTGGGAGTACCCTAGCCAGACC
       IleGluSerTrpGluTyrProSerGlnThr 340       350       360
       CTGACCATCTCCAACAGCCTAATGGTCAGA
       LeuThrIleSerAsnSerLeuMetValArg 370       380       390
       AACTCCAACCAGATCTCTGAGAAGCTCAGC
       AsnSerAsnGlnIleSerGluLysLeuSer 400       410       420
       GACTCTAAAGTGGGCATCAACCTGCTCATC
       AspLeuLysValGlyIleAsnLeuLeuIle 430       440       450
       GAGGGGAGCCAGGAAGGGGTACTGAGCCTG
       GluGlySerGlnGluGlyValLeuSerLeu 460       470       480
       GATGACAATGACTCTCAGCATCTGCCCCCC
       AspAspAsnAspSerGlnHisLeuProPro 490       500       510
       TACGGGAACTACTACCAGAACCTGGGGGGC
       TyrGlyAsnTyrTyrGlnAsnLeuGlyGly 520       530       540
       GACGGCAACGTCAGGAGGAACTACGAACTG
       AspGlyAsnValArgArgAsnTyrGluLeu 550       560       570
       TTGGCCTGCTTCAAGAAGGACATGCATAAG
       LeuAlaCysPheLysLysAspMetHisLys 580       590       600
       GTTGAGACCTACCTGACCGTCGCTAAGTGC
       ValGluThrTyrLeuThrValAlaLysCys 610       620       630
       AGGAAGTCACTGGAGGCCAACTGCACTCTGTAA.
       ArgLysSerLeuGluAlaAsnCysThrLeu***
```

2. A microorganism containing a recombinant DNA plasmid wherein a DNA consisting essentially of a DNA coding for a fish growth hormone polypeptide is incorporated; said growth hormone polypeptide having the peptide sequence:

```
       10        20        30
ATGGGACAAGTGTTTCTGCTGATGCCAGTC
MetGlyGlnValPheLeuLeuMetProVal 40        50        60
       TTACTGGTCAGTTGTTTCCTGAGTCAAGGG
       LeuLeuValSerCysPheLeuSerGlnGly 70        80        90
       GCAGCGATAGAAAACCAACGGCTCTTCAAC
       AlaAlaIleGluAsnGlnArgLeuPheAsn 100       110       120
       ATCGCGGTCAGTCGGGTGCAACATCTCCAC
       IleAlaValSerArgValGlnHisLeuHis 130       140       150
       CTATTGGCTCAGAAAATGTTCAATGACTTT
       LeuLeuAlaGlnLysMetPheAsnAspPhe 160       170       180
       GACGGTACCCTGTTGCCTGATGAACGAGA
       AspGlyThrLeuLeuProAspGluArgArg 190       200       210
       CAGCTGAACAAGATATTCCTGCTGGACTTC
       GlnLeuAsnLysIlePheLeuLeuAspPhe
```

-continued

```
        220        230        240
TGTAACTCTGACTCCATCGTGAGCCCAGTC
CysAsnSerAspSerIleValSerProVal 250        260        270
GACAAGCAGGAGACTCAGAAGAGTTCAGTC
AspLysGlnGluThrGlnLysSerSerVal 280        290        300
CTGAAGCTGCTCCACATTTCTTTCCGTCTG
LeuLysLeuLeuHisIleSerPheArgLeu 310        320        330
ATTGAATCCTGGGAGTACCCTAGCCAGACC
IleGluSerTrpGluTyrProSerGlnThr 340        350        360
CTGACCATCTCCAACAGCCTAATGGTCAGA
LeuThrIleSerAsnSerLeuMetValArg 370        380        390
AACTCCAACCAGATCTCTGAGAAGCTCAGC
AsnSerAsnGlnIleSerGluLysLeuSer 400        410        420
GACTCTAAAGTGGGCATCAACCTGCTCATC
AspLeuLysValGlyIleAsnLeuLeuIle 430        440        450
GAGGGGAGCCAGGAAGGGGTACTGAGCCTG
GluGlySerGlnGluGlyValLeuSerLeu 460        470        480
GATGACAATGACTCTCAGCATCTGCCCCCC
AspAspAsnAspSerGlnHisLeuProPro 490        500        510
TACGGGAACTACTACCAGAACCTGGGGGGC
TyrGlyAsnTyrTyrGlnAsnLeuGlyGly 520        530        540
GACGGAAACGTCAGGAGGAACTACGAGTTG
AspGlyAsnValArgArgAsnTyrGluLeu 550        560        570
TTGGCATGCTTCAAGAAGGACATGCACAAG
LeuAlaCysPheLysLysAspMetHisLys 580        590        600
GTCGAGACCTACCTGACCGTCGCCAAGTGC
ValGluThrTyrLeuThrValAlaLysCys 610        620        630
AGGAAGTCACTGGAGGCCAACTGCACTCTGTAG
ArgLysSerLeuGluAlaAsnCysThrLeu***
``` or

```
        10         20         30
ATGGGACAAGTGTTTCTGCTGATGCCAGTC
MetGlyGlnValPheLeuLeuMetProVal 40         50         60
TTACTGGTCAGTTGTTTCCTGAGTCAAGGG
LeuLeuValSerCysPheLeuSerGlnGly 70         80         90
GCGGCGATGGAAAACCAACGGCTCTTCAAC
MetAlaMetGluAsnGlnArgLeuPheAsn 100        110        120
ATCGTGGTCAACCGGGTGCAACACCTCCAC
IleValValAsnArgValGlnHisLeuHis 130        140        150
CTATTGGCTCAGAAAATGTTCAACGACTTT
LeuLeuAlaGlnLysMetPheAsnAspPhe 160        170        180
GAAGGCACCCTGTTGTCTGATGAACGCAGA
GluGlyThrLeuLeuSerAspGluArgArg
```

-continued

```
        190        200        210
CAGCTGAACAAGATATTCCTGCTGGACTTC
GlnLeuAsnLysIlePheLeuLeuAspPhe 220        230        240
TGTAACTCTGACTCCATCGTGAGCCCCATC
CysAsnSerAspSerIleValSerProIle 250        260        270
GACAAGCACGAGACTCAGAAGAGTTCAGTC
AspLysGlnGluThrGlnLysSerSerVal 280        290        300
CTGAAGCTGCTCCATATCTCTTTCCGCCTG
LeuLysLeuLeuHisIleSerPheArgLeu 310        320        330
ATTGAATCCTGGGAGTACCCTAGCCAGACC
IleGluSerTrpGluTyrProSerGlnThr 340        350        360
CTGACCATCTCCAACAGCCTAATGGTCAGA
LeuThrIleSerAsnSerLeuMetValArg 370        380        390
AACTCCAACCAGATCTCTGAGAAGCTCAGC
AsnSerAsnGlnIleSerGluLysLeuSer 400        410        420
GACTCTAAAGTGGGCATCAACCTGCTCATC
AspLeuLysValGlyIleAsnLeuLeuIle 430        440        450
GAGGGGAGCCAGGAAGGGGTACTGAGCCTG
GluGlySerGlnGluGlyValLeuSerLeu 460        470        480
GATGACAATGACTCTCAGCATCTGCCCCCC
AspAspAsnAspSerGlnHisLeuProPro 490        500        510
TACGGGAACTACTACCAGAACCTGGGGGGC
TyrGlyAsnTyrTyrGlnAsnLeuGlyGly 520        530        540
GACGGCAACGTCAGGAGGAACTACGAACTG
AspGlyAsnValArgArgAsnTyrGluLeu 550        560        570
TTGGCCTGCTTCAAGAAGGACATGCATAAG
LeuAlaCysPheLysLysAspMetHisLys 580        590        600
GTTGAGACCTACCTGACCGTCGCTAAGTGC
ValGluThrTyrLeuThrValAlaLysCys 610        620        630
AGGAAGTCACTGGAGGCCAACTGCACTCTGTAA.
ArgLysSerLeuGluAlaAsnCysThrLeu***
```

3. A recombinant DNA plasmid wherein a DNA codinhg for a fish growth hormone polypeptide is incorporated; said fish growth hormone polypeptide having the peptide sequence:

```
        10         20         30
ATGGGACAAGTGTTTCTGCTGATGCCAGTC
MetGlyGlnValPheLeuLeuMetProVal 40         50         60
TTACTGGTCAGTTGTTTCCTGAGTCAAGGG
LeuLeuValSerCysPheLeuSerGlnGly 70         80         90
GCAGCGATAGAAAACCAACGGCTCTTCAAC
AlaAlaIleGluAsnGlnArgLeuPheAsn
```

-continued

```
         100           110           120
ATCGCGGTCAGTCGGGTGCAACATCTCCAC
IleAlaValSerArgValGlnHisLeuHis 130           140           150
CTATTGGCTCAGAAAATGTTCAATGACTTT
LeuLeuAlaGlnLysMetPheAsnAspPhe 160           170           180
GACGGTACCCTGTTGCCTGATGAACGCAGA
AspGlyThrLeuLeuProAspGluArgArg 190           200           210
CAGCTGAACAAGATATTCCTGCTGGACTTC
GlnLeuAsnLysIlePheLeuLeuAspPhe 220           230           240
TGTAACTCTGACTCCATCGTGAGCCCAGTC
CysAsnSerAspSerIleValSerProVal 250           260           270
GACAAGCAGGAGACTCAGAAGAGTTCAGTC
AspLysGlnGluThrGlnLysSerSerVal 280           290           300
CTGAAGCTGCTCCACATTTCTTTCCGTCTG
LeuLysLeuLeuHisIleSerPheArgLeu 310           320           330
ATTGAATCCTGGGAGTACCCTAGCCAGACC
IleGluSerTrpGluTyrProSerGlnThr 340           350           360
CTGACCATCTCCAACAGCCTAATGGTCAGA
LeuThrIleSerAsnSerLeuMetValArg 370           380           390
AACTCCAACCAGATCTCTGAGAAGCTCAGC
AsnSerAsnGlnIleSerGluLysLeuSer 400           410           420
GACTCTAAAGTGGGCATCAACCTGCTCATC
AspLeuLysValGlyIleAsnLeuLeuIle 430           440           450
GAGGGGAGCCAGGAAGGGGTACTGAGCCTG
GluGlySerGlnGluGlyValLeuSerLeu 460           470           480
GATGACAATGACTCTCAGCATCTGCCCCCC
AspAspAsnAspSerGlnHisLeuProPro 490           500           510
TACGGGAACTACTACCAGAACCTGGGGGGC
TyrGlyAsnTyrTyrGlnAsnLeuGlyGly 520           530           540
GACGGAAACGTCAGGAGGAACTACGAGTTG
AspGlyAsnValArgArgAsnTyrGluLeu 550           560           570
TTGGCATGCTTCAAGAAGGACATGCACAAG
LeuAlaCysPheLysLysAspMetHisLys 580           590           600
GTCGAGACCTACCTGACCGTCGCCAAGTGC
ValGluThrTyrLeuThrValAlaLysCys 610           620           630
AGGAAGTCACTGGAGGCCAACTGCACTCTGTAG
ArgLysSerLeuGluAlaAsnCysThrLeu***
``` or

```
         10            20            30
ATGGGACAAGTGTTTCTGCTGATGCCAGTC
MetGlyGlnValPheLeuLeuMetProVal 40            50            60
TTACTGGTCAGTTGTTTCCTGAGTCAAGGG
LeuLeuValSerCysPheLeuSerGlnGly
```

-continued

```
         70            80            90
GCGGCGATGGAAAACCAACGGCTCTTCAAC
MetAlaMetGluAsnGlnArgLeuPheAsn 100           110           120
ATCGTGGTCAACCGGGTGCAACACCTCCAC
IleValValAsnArgValGlnHisLeuHis 130           140           150
CTATTGGCTCAGAAAATGTTCAACGACTTT
LeuLeuAlaGlnLysMetPheAsnAspPhe 160           170           180
GAAGGCACCCTGTTGTCTGATGAACGCAGA
GluGlyThrLeuLeuSerAspGluArgArg 190           200           210
CAGCTGAACAAGATATTCCTGCTGGACTTC
GlnLeuAsnLysIlePheLeuLeuAspPhe 220           230           240
TGTAACTCTGACTCCATCGTGAGCCCCATC
CysAsnSerAspSerIleValSerProIle 250           260           270
GACAAGCACGAGACTCAGAAGAGTTCAGTC
AspLysGlnGluThrGlnLysSerSerVal 280           290           300
CTGAAGCTGCTCCATATCTCTTTCCGCCTG
LeuLysLeuLeuHisIleSerPheArgLeu 310           320           330
ATTGAATCCTGGGAGTACCCTAGCCAGACC
IleGluSerTrpGluTyrProSerGlnThr 340           350           360
CTGACCATCTCCAACAGCCTAATGGTCAGA
LeuThrIleSerAsnSerLeuMetValArg 370           380           390
AACTCCAACCAGATCTCTGAGAAGCTCAGC
AsnSerAsnGlnIleSerGluLysLeuSer 400           410           420
GACTCTAAAGTGGGCATCAACCTGCTCATC
AspLeuLysValGlyIleAsnLeuLeuIle 430           440           450
GAGGGGAGCCAGGAAGGGGTACTGAGCCTG
GluGlySerGlnGluGlyValLeuSerLeu 460           470           480
GATGACAATGACTCTCAGCATCTGCCCCCC
AspAspAsnAspSerGlnHisLeuProPro 490           500           510
TACGGGAACTACTACCAGAACCTGGGGGGC
TyrGlyAsnTyrTyrGlnAsnLeuGlyGly 520           530           540
GACGGCAACGTCAGGAGGAACTACGAACTG
AspGlyAsnValArgArgAsnTyrGluLeu 550           560           570
TTGGCCTGCTTCAAGAAGGACATGCATAAG
LeuAlaCysPheLysLysAspMetHisLys 580           590           600
GTTGAGACCTACCTGACCGTCGCTAAGTGC
ValGluThrTyrLeuThrValAlaLysCys 610           620           630
AGGAAGTCACTGGAGGCCAACTGCACTCTGTAA.
ArgLysSerLeuGluAlaAsnCysThrLeu***
```

4. The recombinant DNA according to claim 3 which is named plasmid pSGH1 or pSGH14.

5. The microorganism according to claim 2, wherein the microorganism belongs to *Escherichia coli.*

* * * * *